United States Patent [19]

Skaliotis

[11] Patent Number: 4,840,798

[45] Date of Patent: Jun. 20, 1989

[54] ASTRINGENT GEL COMPOSITION AND METHOD FOR USE

[75] Inventor: Dennis A. Skaliotis, New Bedford, Mass.

[73] Assignee: Theon, Inc., New Bedford, Mass.

[21] Appl. No.: 224,809

[22] Filed: Jul. 27, 1988

[51] Int. Cl.$^4$ .......................... A61K 9/14; A61K 9/16; A61K 31/28

[52] U.S. Cl. .................................... 424/488; 424/486; 514/492

[58] Field of Search ............... 514/827, 828, 848, 944, 514/557, 781; 424/154, 486, 488, 492

[56] References Cited

U.S. PATENT DOCUMENTS

| | | | | |
|---|---|---|---|---|
| 3,856,941 | 12/1974 | Turner | ................................. | 424/154 |
| 4,246,285 | 1/1981 | Van Duzee | .......................... | 514/781 |
| 4,618,491 | 10/1986 | Kanematue et al. | ................... | 424/81 |

OTHER PUBLICATIONS

AMA Drug Evaluations, Fifth Edition, p. 139z (1983).
Martindale, The Extra Pharmacopoeia, 28th Edition, p. 284 (1982).
Physician's Desk Reference, 40th Edition, p. 1397, (1986).
Handbook of Nonprescription Drugs, Eighth Edition, p. 435, (1983).

*Primary Examiner*—Douglas W. Robinson
*Assistant Examiner*—Roger Gobrogge
*Attorney, Agent, or Firm*—Perman & Green

[57] ABSTRACT

The present invention provides a stable astringent gel composition containing pharmaceutically acceptable dosage levels of Burow's solution which remains stable over extended periods of storage and which can readily be applied to the skin to alleviate inflammatory conditions, erythema, chapping and minor skin irritations. The composition comprises a mixture of Burow's solution, a thickening or gelling agent, at least one glycol and polyglycol, dispersed in gypsum saturated purified water. The gel is adapted for application directly to affected areas of the skin to bind or tighten the soft tissue and also to tone and moisturize the skin.

14 Claims, No Drawings

ASTRINGENT GEL COMPOSITION AND METHOD FOR USE

BACKGROUND OF THE INVENTION

1. Field of Invention

The present invention relates to aluminum containing astringent gel compositions and a method for their use.

2. Description of the Prior Art

Aluminum acetate solution, also referred to as Burow's solution, has long been known and used as an astringent when applied to the skin. It is approved for use by the US Food and Drug Administration dispensed as a 2.5 to 5% by weight clear solution of aluminum acetate (triacetate) for use as a wet dressing, compress or soak for relief of inflammatory conditions and minor skin irritations. Burow's solution may be prepared by reacting aluminum sulfate, calcium carbonate and 6 molar acetic acid to form aluminum subacetate topical solution (also referred to as monobasic aluminum diacetate) and a precipitate of calcium sulfate. The calcium salt precipitate is removed by filtration and the filtrate is converted to aluminum acetate solution (Burow's solution) by the addition of acetic acid. Other methods for the preparation of Burow's solution include treatment of dibasic aluminum monoacetate with glacial acetic acid and the methods disclosed in U.S. Pat. Nos. 2,824,042 and 2,827,420.

It is generally recommended that Burow's solution be freshly prepared before use because it tends to become unstable over prolonged periods of standing and tends to lose its potency. This loss in potency is due to the precipitation of the more basic aluminum salts.

It is also common in the prior art to prepare mediciment formulations in the form of a gel for application to the skin. For example, U.S. Pat. No. 3,856,941 discloses an astringent gel formulation based on a mixture of astringent salts such as aluminum and zinc, zirconium or magnesium salts, and further including a gelling agent and a glycol. The patent indicates that the stability of the formulation is enhanced by combining two or more such salts and formulating them into a gel at relatively high concentrations of about 13 to 18% by weight.

However, the requirement of the usage of such a mixture of salts at relatively high concentration in the gel formulation to achieve stability can give rise to other problems including tolerance or irritation of the skin to such preparations due to the high salt concentration.

Accordingly it is an object of this invention to provide a formulation of Burow's solution in gel form for convenient application to the skin.

Another object is to provide a formulation of Burow's solution as a gel which remains stable over extended periods of storage.

Yet another object of the invention is to provide an astringent formulation for application to the skin, particularly to the hands, for relief of inflammatory skin conditions, erythema. chapping and minor ulcerations of the skin.

SUMMARY OF THE INVENTION

The present invention provides a stable astringent gel composition containing pharmaceutically acceptable dosage levels of Burow's solution which remains stable over extended periods of storage and which can readily be applied to the skin to alleviate inflammatory conditions, erythema, chapping and minor skin irritations.

The composition comprises a mixture of Burow's solution, a thickening or gelling agent, at least one glycol and/or polyglycol, dispersed in gypsum saturated purified water. The gel is adapted for application directly to affected areas of the skin to bind or tighten the soft tissue and also to tone and moisturize the skin.

DETAILED DESCRIPTION OF THE INVENTION

The principal active ingredient in the gel composition of the present invention is Burow's solution. This aqueous solution of aluminum acetate may be prepared by any of the well known techniques as described hereinabove. Potent, freshly prepared Burow's solution comprises predominantly aluminum acetate present as the triacetate, most commonly present at a concentration of about 2.0 to about 7.0% by weight, more preferably from about 2.5 to about 5% by weight, the balance being water.

Gelling agents which are useful in the preparation of the astringent gel in accordance with the present invention include those agents known in the art and used in gels to be applied to the skin. Preferably the gelling agent used in the present invention is a non-ionic gelling agent and therefore exhibits none or only slight sensitivity to multivalent cations such as aluminum. Ionic gelling agents can lead to crosslinking of aluminum and consequent precipitation of ionic hydrocolloids. The most preferred gelling agents are cellulose ethers or esters having a molecular weight within the range of about 10,000 to about 30,000, most preferably methyl cellulose ethers. Also suitable as a gelling agent are polyvinyl alcohols having an average molecular weight within the range of about 15,000 to about 90,000 and containing up to about 15% acetate groups.

Non-ionic gelling agents such as described above can lead to an undesirable foaming or whitening of the gel composition after application to the skin due to their tendency to reduce surface tension. It has been found that the inclusion of minor amounts of a lower poly alkylene glycol into the formulation will eliminate this foaming or whitening before it can occur by replacing the gelling agent at the air/water interface after application to the skin. Preferred polyols are polyethylene glycol, polypropylene glycol and polybutylene glycol, and mixtures thereof.

The preferred composition of this invention also includes a $C_2$ to $C_4$ alkylene glycol such as ethylene glycol, propylene glycol, 1,3 butylene glycol, glycerol, or mixtures thereof. It has been found that the presence of the lower alkylene glycol serves a two fold purpose: to impart a moisturizing effect to the skin after application of the gel thereby extending the time that the skin remains wet, and to act as a solvent for the polyol thereby enhancing its anti-foaming and anti-whitening effect.

The balance of the aqueous component of the gel formulation is a solution of gypsum saturated water, preferably purified distilled water. This saturated solution imparts stability to the aluminum acetate active ingredient present in the gel and tends to prevent a loss in potency of the astringent gel over prolonged periods of storage. Preferably, the gypsum is used in the form of calcium sulfate, NF grade. The saturated solution may be prepared by boiling a 5% dispersion of gypsum (or calcium sulfate) in purified water (USP) for a period of at least about 10 minutes. The solution/dispersion is then cooled to room temperature and filtered to remove the non-dissolved salt. The resultant saturated solution assays at about 0.2% by weight dissolved calcium sulfate.

It has also been found that the presence of the purified water saturated with calcium sulfate in the gel also imparts a cooling effect when the gel is applied to the skin.

Preferably, the astringent gel composition of the present invention consists essentially of the above named ingredients, but it may also contain other ingredients which do not detract from either the astringent effect or the stability of the gel.

Examples of such ingredients include dyes, perfumes, non-ionic emulsifiers, healing agents, antiseptic, antibacterial, antibiotic and/or germicidal substances, and keratolytic agents.

The gel composition is formulated to have a pH in the range of about 3.5 to about 5.5, preferably from 4.0 to 4.5.

The preferred proportion of the ingredients present in the gel may range generally from about 40 to about 80% by weight of aluminum acetate solution, from about 0.5 to about 4.0% by weight of gelling agent, from about 0.05 to about 2.0% by weight of lower polyalkylene glycol, from about 5 to about 25% by weight of $C_2$ to $C_4$ alkylene glycol, and the balance of gypsum saturated water is generally present in the range of about 15 to about 40% by weight. The concentration of aluminum acetate present in the aluminum acetate solution (Burow's solution) may generally range between about 2 to about 7% by weight, more preferably about 4.5% by weight.

The following example is illustrative of the invention.

EXAMPLE 1

An astringent gel composition having the following composition was prepared:

| INGREDIENT | % BY WEIGHT | |
|---|---|---|
| propylene glycol | 20.0 | |
| hydroxypropyl methylcellulose 2208 | 1.3 | Sold as Methocel K-100M by Dow Chemical Corp. |
| polypropylene glycol | 0.20 | Sold as Polyglycol P-1200 by Dow Chemical Corp. |
| aluminum acetate solution | 60.00 | Containing about 4.5% by weight aluminum triacetate. |
| purified water (gypsum extracted) | 18.00 | Containing about 0.2% by weight dissolved calcium sulfate. |
| FDC Blue #1 (0.1% aqueous soln) | 0.50 | |
| Total | 100.00 | |

The aluminum acetate solution was prepared by dissolving dibasic aluminum acetate in distilled water and adding sufficient glacial acetic acid to form aluminum triacetate at about a 4.5% by weight concentration. The resulting solution is then filtered to remove insolubles. The purified gypsum extracted water was prepared by dispersing about 5% by weight of calcium sulfate (NF grade) in purified water, boiling for about 10 minutes, cooling and filtering to remove insolubles. The resulting saturated solution of calcium sulfate had a content of calcium sulfate of about 0.2% by weight.

The gel containing the aforementioned ingredients was prepared by first dissolving the polypropylene glycol in the propylene glycol and mixing until uniform. Next the methyl cellulose gelling agent is added slowly to this mixture with adequate stirring until a uniform dispersion is obtained. This dispersion is then added to a blend of aluminum acetate solution, dye and gypsum extracted water and mixed until the dispersion is uniform and gelatinization is complete.

The gel is then ready for packaging and for use.

CLINICAL TRIAL

Procedure

A group of 30 female subjects between the ages of 18 and 65 having erythema and dryness/chapping of both hands was selected for evaluation.

The subjects were provided with the gel of the present invention for application twice daily to a single hand, in the evening and in the morning, over a period of 5 days for a total of nine applications. The panelists were issued nine capped 1 ml syringes each containing about 0.5 grams of the gel, and a supply of rubber gloves. The panelists were instructed to place the plastic glove on the hand opposite the hand to be treated, to empty the entire contents of the syringe on the back of the hand to be treated and to gently spread and to gently massage the gel into the skin of the back of the hand to be treated, between the distal knuckles and wrist crease, and into the interdigital spaces, until the gel was absorbed.

The panelists were also instructed to bath once per day and to wash both the hands with IVORY ® soap four times per day at selected intervals.

Both prior to and subsequent to the clinical evaluation, the degree of erythema and dryness/chapping of the back of the panelists hands were evaluated according to the following five point scoring scales:

| (a) | Erythema | Score |
|---|---|---|
| | None | 0 |
| | Pink | 1 |
| | Red | 2 |
| | Fiery red | 3 |
| | Fiery red and raw; hemorrhagic areas | 4 |
| (b) | Dryness/Chapping | |
| | Smooth, soft, good turgor (and/or slight drying but no scaling) | 0 |
| | Definite dryness with slight scaling | 1 |
| | Definite dryness and chapping with scaling and some flaking | 2 |
| | Severe dryness and chapping with definite scaling and flaking, and some rigidity and cracking | 3 |
| | Very severe dryness with roughness, severe scaling and wide cracking, rigidity and eczematous appearance | 4 |

Each of the selected 30 panelists had a rating in each category of at least 2 prior to being selected for the clinical treatment.

Clinical evaluation scores for erythema and dryness/chapping are summarized in Table 1. For both the untreated and treated hands there are reductions (improvements) in the scores for erythema and dryness/chapping over the course of the test period. These improvements for the treated hand are approximately four times greater than those for the untreated hand, and are satistically significant at the 99% confidence level. The relatively small score changes for the untreated hand are not statistically significant. Even after correction of the changes in treated hand scores by the corresponding changes in untreated hand scores, the improvement in treated hand scores is still of statistical significance at the same confidence level.

TABLE 1

| | CLINICAL EVALUATION SCORES | | | |
|---|---|---|---|---|
| Time | Untreated | Treated | Treated | Corrected[1] |
| | M ± SD[b] | M ± SD | Δ | t[c] |
| A. Erythema | | | | |
| Initial (Baseline) | 2.57 ± 0.63 | 2.57 ± 0.68 | | |
| Final (End Study) | 2.43 ± 0.68 | 2.00 ± 0.64 | | |
| Δ | 0.13 ± 0.57 | 0.57 ± 0.68 | 0.43 ± 0.57 | 4.18** |
| t | 1.28 | 4.57** | | |
| B. Dryness/Chapping | | | | |
| Initial (Baseline) | 2.63 ± 0.72 | 2.63 ± 0.67 | | |
| Final (End Study) | 2.37 ± 0.85 | 1.60 ± 0.77 | | |
| Δ | 0.27 ± 0.69 | 1.03 ± 0.7 | 0.77 ± 0.82 | 5.14** |
| t | 2.11 | | | |

FOOTNOTES:
[a]The difference (Δ) between initial and final mean values of the treated hand corrected for the difference (Δ) between the initial and final mean values of the untreated hand.
[b]Mean ± standard deviation.
[c]Student's t test value with the statistical significance of the difference (Δ) between mean values at the 95% confidence level indicated by *, and at the 99% confidence level by **.

It is to be understood that the above described embodiments of the invention are illustrative only and that modifications throughout may occur to those skilled in the art.

What I claim is:

1. An astringent gel composition for treating inflammatory skin conditions, erythema, chapping and skin irritations comprising a uniform mixture of:
   (a) an aqueous solution of aluminum acetate containing from about 2.0 to about 7.0% by weight of aluminum, acetate,
   (b) a gelling agent present at a level of from about 0.5 to about 4.0% by weight,
   (c) a lower polyalkylene glycol present at a level of from about 0.5 to about 2.0% by weight,
   (d) a $C_2$ to $C_4$ alkylene glycol present at a level of from about 5 to about 25% by weight, and
   (e) a saturated aqueous solution of calcium sulfate,
   said aluminum acetate being present in therapeutically effective amounts and said calcium sulfate being present in an amount sufficient to enhance the storage stability of the composition.

2. The composition of claim 1 wherein said aqueous solution of aluminum acetate is present at a level of from about 40 to about 80% by weight.

3. The composition of claim 2 wherein the concentration of aluminum acetate is about 4.5% by weight.

4. The composition of claim 1 wherein said gelling agent is a non-ionic gelling agent.

5. The composition of claim 4 wherein said gelling agent is a methyl cellulose ether.

6. The composition of claim 1 wherein said polyalkylene glycol is polypropylene glycol.

7. The composition of claim 1 wherein said alkylene glycol is propylene glycol.

8. The composition of claim 1 wherein said saturated aqueous solution of calcium sulfate is present at a level of from about 15 to about 40% by weight.

9. The composition of claim 8 wherein the concentration of calcium sulfate in said saturated solution is about 0.2% by weight.

10. The astringent gel composition of claim 1 consisting essentially of a uniform mixture of:
    (a) from about 40 to about 80% by weight of an aqueous solution containing from about 2 to about 7% by weight aluminum acetate;
    (b) from about 0.5 to about 4.0% by weight of methyl cellulose ether;
    (c) from about 0.05 to about 2.0% by weight of polypropylene glycol;
    (d) from about 5 to about 25% by weight of propylene glycol; and
    (e) from about 15 to about 40% by weight of purified water saturated with calcium sulfate.

11. The gel composition of claim 10 consisting essentially of:
    (a) about 60% by weight of an aqueous solution of aluminum acetate;
    (b) about 1.3% by weight of hydroxypropylmethylcellulose;
    (c) about 0.2% by weight of polypropylene glycol;
    (d) about 20% by weight propylene glycol, and
    (e) about 18% by weight of purified water saturated with calcium sulfate.

12. The gel composition of claim 11 wherein said aqueous aluminum acetate solution contains about 4.5% by weight of dissolved aluminum acetate.

13. A method for treating inflammatory skin conditions, erythema, chapping and skin irritations comprising topically applying an effective amount of the gel composition of claim 1 to involved portions of the skin.

14. A method for treating inflammatory skin conditions, erythema, chapping and skin irritations comprising topically applying an effective amount of the gel composition of claim 10 to involved portions of the skin.

* * * * *